(12) United States Patent
Fitch et al.

(10) Patent No.: US 7,263,874 B2
(45) Date of Patent: Sep. 4, 2007

(54) METHODS AND APPARATUS FOR DETERMINING PROPERTIES OF A FLUID

(75) Inventors: Eric Fitch, Arlington, MA (US); Stuart Wenzel, San Francisco, CA (US)

(73) Assignee: BioScale, Inc., Cambridge, MA (US)

( * ) Notice: Subject to any disclaimer, the term of this patent is extended or adjusted under 35 U.S.C. 154(b) by 75 days.

(21) Appl. No.: 11/148,156

(22) Filed: Jun. 8, 2005

(65) Prior Publication Data

US 2006/0277979 A1  Dec. 14, 2006

(51) Int. Cl.
*G01N 11/10* (2006.01)

(52) U.S. Cl. .................................... 73/54.25

(58) Field of Classification Search ............. 73/54.23, 73/54.24, 54.25
See application file for complete search history.

(56) References Cited

U.S. PATENT DOCUMENTS

| | | | | |
|---|---|---|---|---|
| 2,490,452 | A | * | 12/1949 | Mason ......................... 367/142 |
| 2,707,391 | A | * | 5/1955 | McSkimin ................... 73/54.27 |
| 4,847,193 | A | | 7/1989 | Richards et al. ............... 435/6 |
| 4,890,480 | A | | 1/1990 | Young ......................... 73/32 A |
| 5,005,401 | A | | 4/1991 | Pierce et al. ..................... 73/54 |
| 5,074,149 | A | | 12/1991 | Stearns ......................... 73/579 |
| 5,129,262 | A | | 7/1992 | White et al. ................... 73/599 |
| 5,189,914 | A | | 3/1993 | White et al. ................... 73/599 |
| 5,201,215 | A | | 4/1993 | Granstaff et al. ........... 73/54.41 |
| 5,235,235 | A | | 8/1993 | Martin et al. ............ 310/313 D |
| 5,339,051 | A | | 8/1994 | Koehler et al. ................. 331/65 |
| 5,455,475 | A | * | 10/1995 | Josse et al. ............. 310/316.01 |
| 5,456,114 | A | | 10/1995 | Liu et al. ........................ 73/597 |
| 5,668,303 | A | | 9/1997 | Giesler et al. ............. 73/24.06 |
| 5,741,961 | A | | 4/1998 | Martin et al. ................ 73/32 R |
| 5,798,452 | A | | 8/1998 | Martin et al. ................ 73/32 R |
| 5,842,787 | A | | 12/1998 | Kopf-Sill et al. ........... 366/340 |
| 5,869,748 | A | | 2/1999 | Stevenson et al. ......... 73/53.01 |
| 5,889,351 | A | | 3/1999 | Okumura et al. ............ 310/321 |
| 5,892,144 | A | | 4/1999 | Meller et al. .............. 73/64.42 |

(Continued)

FOREIGN PATENT DOCUMENTS

EP    0 816 808 A1    1/1998

(Continued)

OTHER PUBLICATIONS

Zhang et al., "Mode Interference Study of Bulk Acoustic Wave Liquid Sensors," 2001, 2001 IEEE Ultrasonics Symposium, pp. 347-352.*

(Continued)

*Primary Examiner*—Hezron Williams
*Assistant Examiner*—John Fitzgerald
(74) *Attorney, Agent, or Firm*—Proskauer Rose LLP

(57) ABSTRACT

A method and system for determining properties of a fluid involves interacting the fluid with a standing wave in a first state to establish the standing wave in a second state, analyzing an electric signal associated with the standing wave to determine a characteristic associated with the second state, and determining the property of the fluid by comparing the characteristic with a function that associates a plurality of properties with a corresponding plurality of characteristics. The characteristic can include a maximum phase slope, a phase slope associated with a resonant frequency, a maximum magnitude associated with the resonant frequency, the value of the resonant frequency, or any combination thereof.

22 Claims, 5 Drawing Sheets

U.S. PATENT DOCUMENTS

| | | | | |
|---|---|---|---|---|
| 5,932,953 | A | 8/1999 | Drees et al. | 310/324 |
| 5,998,224 | A | 12/1999 | Rohr et al. | 436/526 |
| 6,044,694 | A | 4/2000 | Anderson et al. | 73/54.41 |
| 6,053,041 | A | 4/2000 | Sinha | 73/290 V |
| 6,086,821 | A | 7/2000 | Lee | 422/20 |
| 6,156,181 | A | 12/2000 | Parce et al. | 204/600 |
| 6,189,367 | B1 * | 2/2001 | Smith et al. | 73/19.03 |
| 6,196,059 | B1 | 3/2001 | Kösslinger et al. | 73/61.49 |
| 6,247,354 | B1 | 6/2001 | Vig et al. | 73/54.41 |
| 6,249,025 | B1 | 6/2001 | Tyagi | 436/514 |
| 6,260,408 | B1 | 7/2001 | Vig et al. | 73/64.53 |
| 6,312,383 | B1 | 11/2001 | Lizzi et al. | 600/437 |
| 6,336,353 | B2 | 1/2002 | Matsiev et al. | 73/24.06 |
| 6,393,895 | B1 | 5/2002 | Matsiev et al. | 73/24.06 |
| 6,401,519 | B1 | 6/2002 | McFarland et al. | 73/24.6 |
| 6,412,354 | B1 | 7/2002 | Birchak et al. | 73/861.356 |
| 6,513,365 | B1 * | 2/2003 | Bruetting et al. | 73/32 A |
| 6,551,836 | B1 | 4/2003 | Chow et al. | 436/149 |
| 6,558,944 | B1 | 5/2003 | Parce et al. | 435/287.2 |
| 6,563,588 | B2 * | 5/2003 | Behroozi | 356/477 |
| 6,575,020 | B1 | 6/2003 | de Charmoy Grey et al. | 73/54.23 |
| 6,681,616 | B2 | 1/2004 | Spaid et al. | 73/54.07 |
| 6,779,387 | B2 | 8/2004 | Degertekin | 73/105 |
| 6,817,229 | B2 | 11/2004 | Han et al. | 73/64.53 |
| 6,820,469 | B1 * | 11/2004 | Adkins et al. | 73/54.25 |
| 6,823,720 | B1 * | 11/2004 | Adkins et al. | 73/54.25 |
| 6,837,097 | B2 | 1/2005 | Cunningham et al. | 73/24.06 |
| 6,848,295 | B2 | 2/2005 | Auner et al. | 73/24.06 |
| 6,851,297 | B2 | 2/2005 | Cunningham et al. | 73/24.06 |
| 6,889,560 | B2 | 5/2005 | Sinha | 73/861.25 |
| 6,910,366 | B2 | 6/2005 | Drahm et al. | 73/54.24 |
| 6,943,484 | B2 | 9/2005 | Clark et al. | 310/334 |
| 6,953,977 | B2 | 10/2005 | Mlcak et al. | 257/414 |
| 6,971,259 | B2 | 12/2005 | Gysling | 73/32 A |
| 2003/0134431 | A1 | 7/2003 | Parce et al. | 436/518 |
| 2004/0113522 | A1 | 6/2004 | Nagahara et al. | 310/326 |
| 2004/0200268 | A1 | 10/2004 | Drahm et al. | 73/54.41 |
| 2005/0005676 | A1 | 1/2005 | Crawley et al. | 73/24.01 |
| 2005/0097943 | A1 | 5/2005 | Sinha | 73/61.49 |
| 2005/0160821 | A1 | 7/2005 | Cunningham et al. | 73/652 |
| 2005/0241372 | A1 | 11/2005 | Drahm et al. | 73/54.24 |
| 2005/0264302 | A1 * | 12/2005 | Mohajer et al. | 324/639 |
| 2006/0019330 | A1 | 1/2006 | Laksjmi et al. | 435/34 |
| 2006/0031030 | A1 | 2/2006 | Bennett et al. | 702/50 |

FOREIGN PATENT DOCUMENTS

| | | |
|---|---|---|
| JP | 60 067839 | 4/1985 |
| WO | WO 95/32419 A | 11/1995 |
| WO | WO 2005/114138 A2 | 12/2005 |

OTHER PUBLICATIONS

Durdag, "Measuring Viscosity with Surface Acoustic Wave Sensor," Oct. 1, 2005, Sensors Process Industries, pp. 1-3.*
Alder, Eric L., "Electromechanical Coupling to Lamb and Shear-Horizontal Modes in Piezoelectric Plates," IEEE Transactions on Ultrasonics, Ferroelectrics, and Frequency Control, vol. 36 No. 2 (Mar. 1989) pp. 223-230.
Baer, et al., "Phase Noise Measurements of Flexural Plate Wave Ultrasonic Sensors," IEEE 1991 Ultrasonics Symposium, vol. 1 (1991) pp. 321-326.
Cunningham, et al., "Design, fabrication and vapor characterization of a microfabricated flexural plate resonator sensor and application to integrated sensor arrays," Sensors and Actuators, B 73 (2001) pp. 112-123.
Das, et al., "A Pressure Sensing Acoustic Surface Wave Resonator," IEEE 1976 Ultrasonics Symposium, (Sep. 29-Oct. 1, 1976) pp. 306-308.
Dias, et al., "Frequency/Stress Sensitivity of S.A.W. Resonators," Electronics Letters, vol. 12, No. 22 (Oct. 28, 1976), pp. 580-582.
Gast, Theodor, "Sensors with oscillating elements," Journal of Physics E:Scientific Instruments, vol. 18, No. 9 (Sep. 1985) pp. 783-789.
Grate, et al., "Flexural Plate Wave Devices for Chemical Analysis," Analytical Chemistry, vol. 63, No. 15 (Aug. 1, 1991), pp. 1552-1561.
Grate, et al., "Frequency-Independent and Frequency-Dependent Polymer Transitions Observed on Flexural Plate Wave Ultrasonic Sensors," Analytical Chemistry, vol. 64, No. 4 (Feb. 15, 1992), pp. 413-423.
Hauden, D., "Miniaturized Bulk and Surface Acoustic Wave Quartz Oscillators Used as Sensors," IEEE Transactions on Ultrasonics, Ferroelectrics, and Frequency Control, vol. UFFC-34, No. 2 (Mar. 1987), pp. 253-258.
Höök, et al., "Energy Dissipation Kinetics for Protein and Antibody—Antigen Adsorption under Shear Oscillation on a Quartz Crystal Microbalance," Langmuir, vol. 14, No. 4 (1998), pp. 729-734.
Rodahl, et al., "Quartz crystal microbalance setup for frequency and Q-factor measurements in gaseous and liquid environments," Rev. Sci. Instrum., vol. 666, No. 7 (Jul. 1995), pp. 3924-3930.
Höök, et al., "Variations in Coupled Water, Viscoelastic Properties, and Film Thickness of a Mepf-1 Protein Film during Adsorption and Cross-Linking: A Quartz Crystal Microbalance with Dissipation Monitoring, Ellipsometry, and Surface Plasmon Resonance Study," Analytical Chemistry, vol. 73, No. 24 (Dec. 15, 2001), pp. 5796-5804.
Howe, Roger T., "Resonant Microsensors," TRANSDUCERS, '87, pp. 843-848.
Jain, et al., "Measurement of Temperature and Liquid Viscosity Using Wireless Magneto-Acoustic/Magneto-Optical Sensors," IEEE Transactions on Magnetics, vol. 37, No. 4 (Jul. 2001), pp. 2767-2769.
Johannsmann, et al., "Visco-elastic properties of thin films probed with a quartz crystal resonator," Makromolekulare Chemie, Macromolecular Symposia, vol. 46 (1991), pp. 247-251.
Josse, et al., "Analysis of Piezoelectric Bulk-Acoustic-Wave Resonators as Detectors in Viscous Conductive Liquids," IEEE Transactions on Ultrasonics, Ferroelectrics, and Frequency Control, vol. 37, No. 5 (Sep. 1990), pp. 359-368.
Langdon, R. M., "Resonator sensors—a review," Journal of Physics E Scientific Instruments, vol. 18, No. 2 (Feb. 1985), pp. 103-115.
Lewis, M. F., "Surface acoustic wave devices and applications," Ultrasonics (May 1974), pp. 115-123.
Martin, et al., "Surface acoustic wave response to changes in viscoelastic film properties," Applied Physics Letters, vol. 57, No. 18 (Oct. 29, 1990), pp. 1867-1869.
Neumeister, et al., "A SAW Delay-line Oscillator as a High-resolution Temperature Sensor," Sensors and Actuators, vol. A22, Nos. 1-3 (Mar. 1990), pp. 670-672.
Nomura, et al., "Measurement of Acoustic Properties of Liquids Using SH-Type Surface Acoustic Waves," IEEE Ultrasonics Symposium (1990), pp. 307-310.
Reeder, et al., "Surface-Acoustic-Wave Pressure and Temperature Sensors," Proceedings of the IEEE, vol. 64, No. 5 (May 1976), pp. 754-756.
Ricco, et al., "Acoustic wave viscosity sensor," Applied Physics Letters, vol. 50, No. 21 (May 25, 1987), pp. 1474-1476.
Tang, William Chi-Keung, Ph.D., "Electrostatic comb drive for resonant sensor and actuator applications," Ph.D. Thesis submitted at University of California, Berkeley (approved Nov. 21, 1990).
Toda, Kohji, "Lamb-wave delay lines with interdigital electrodes," Journal of Applied Physics, vol. 44, No. 1 (Jan. 1973), pp. 56-62.
Voinova, et al., "Viscoelastic Acoustic Response of Layered Polymer Films at Fluid-Sold Interfaces: Continuum Mechanics Approach," Department of Theoretical Physics, Kharkov State University, Kharkov, 310077, Ukraine, (1999), pp. 391-396.
Wenzel, et al., "Analytic comparison of the sensitivities of bulk-wave, surface-wave, and flexural plate-wave ultrasonic gravimetric sensors," Applied Physics Letters, vol. 54, No. 20 (May 15, 1989), pp. 1976-1978.
Wenzel, Stuart William, Ph.D., "Applications of ultrasonic lamb waves," Ph.D. Thesis submitted at University of California, Berkeley (approved Apr. 28, 1992).

White, et al., "Direct Piezoelectric Coupling to Surface Elastic Waves," Applied Physics Letters, vol. 7, No. 12 (Dec. 15, 1965), pp. 314-316.

White, et al., "Plate-Mode Ultrasonic Oscillator Sensors," IEEE Transactions on Ultrasonics Ferroelectrics, and Frequency Control, vol. UFFC-34, No. 2 (Mar. 1987), pp. 162-171.

White, Richard M., "Thermoelastic Coupling to Lamb Waves," IEEE Ultrasonics Symposium Proceedings, vol. 1 (Nov. 17-19, 1986), pp. 411-415.

"Thickness Shear Mode Resonators", Microsensors, Sandia National Laboratories, (retrieved on May 23, 2005) http://www.sandia.gov/mstc/technologies/microsensors/thicknessshearmode.html>, pp. 1-3.

"QCM-D Technology", Q-Sense, (retrieved on May 23, 2005), http://www.q-sense.com/main.qcmd_tech.html>, pp. 1-2.

"Tone Burst Generators in Research", NDT Resource Center, (retrieved on May 3, 2005), http://www.ndt-ed.org/EducationResources/CommunityCollege/Ultrasonics/EquipmentTrans/toneburst.htm>, pp. 1-2.

"Magnetically-Excited Flexural Plate Wave Device" Microsensors, Sandia National Laboratories, (retrieved on May 2, 2005), http://www.sandia.gov/mstc/technologies/microsensors/flexural.html>, pp. 1-2.

A. F. Collings et al., "Biosensors: recent advances," Rep. Prog. Phys., vol. 60, 1997, pp. 1397-1445.

B. J. Costello et al., "A Flexural-Plate-Wave Microbial Sensor," IEEE, 0-7803-0456-X/92, pp. 69-72.

BiODE, Technical White Paper # 1, available at "http://www.biode.com", pp. 1-4, (last visited Jun. 13, 2006).

Boston MicroSystems—Fluid Sensors, fluid sensors tab, at "http://www.bostonmicrosystems.com/fluidsensors.html" (last visited May 25, 2005), pp. 1-3.

D. S. Ballantine, Jr. et al., "Acoustic Wave Sensors—*Theory, Design, and Physico-Chemical Applications*," Academic Press, New York, 1997.

D. Sparks et al., "Measurement of density and chemical concentration using a microfluidic chip," Lab Chip, vol. 3, 2003, pp. 19-21.

Giesler et al., "Electrostatic excitation and capacitive detection of flexural plate-waves," Sensors and Actuators A, vol. 36, 1993, pp. 113-119.

I. Dion, "A Stand-alone Acoustic Wave Sensor for Liquid Viscosity Measurement," Master's Thesis, Institute of Micro-Electro-Mechanical-System of Engineering, 2003.

J. L. Dohner, "The Contribution of Radiation and Viscous Loss in a Fluid Loaded Flexural Plate Wave Sensor," Journal of Sound and Vibration, vol. 217, No. 1, 1998, pp. 113-126.

N. Nguyen et al., "AcousticStreaming in Micromachined Flexural Plate Wave Devices: Numerical Simulation and Experimental Verification," IEEE Transactions on Ultrasonics, Ferroelectrics, and Frequency Control, vol. 47, No. 6, Nov. 2000, pp. 1463-1471.

S. Shi-Hui et al., "Bulk acoustic wave sensor for investigating hemorheoloical characteristics of plasma and its coagulation," J. Biochem. Biophys. Methods, vol. 31 (1996), pp. 135-143.

Loiselle et al., "Viscosity measurements of viscous liquids using magnetoelastic thick-film sensors", Review of Scientific Instruments, vol. 71, No. 3, Mar. 2000, pp. 1441-1446. XP002403813.

Herrmann et al., "Microacoustic sensors for liquid monitoring", Sensors Update, vol. 9, Jun. 13, 2001, pp. 105-160. XP002403814.

Patel et al., "Real-Time Detection of Organic Compounds in Liquid Environments Using Polymer-Coated Thickness Shear Mode Quartz Resonators", Anal. Chem., vol. 72, 2000, pp. 4888-4898. XP002403815.

International Search Report for PCT Patent Application No. PCT/US2006/022191, Mailed on Nov. 9, 2006.

* cited by examiner

METHODS AND APPARATUS FOR DETERMINING PROPERTIES OF A FLUID

GOVERNMENT SUPPORT

This invention was made with government support under Contract Number N00014-04-M-0310 awarded by the United States Department of the Navy. The government may have certain rights in the invention.

FIELD OF THE INVENTION

The invention relates generally to determining properties of a fluid and in particular, to determining properties of a fluid by analyzing an interaction of the fluid with a standing wave associated with a surface of a resonant device.

BACKGROUND

Fluids generally are characterized by multiple properties, for example, viscosity, density, temperature, chemical composition, phase (e.g., gas or liquid), compressibility and pressure that can be measured and determined experimentally. Determining fluid properties is important for a wide variety of industrial applications. For example, time-based maintenance of heavy equipment or machinery involves maintaining or changing fluids on a fixed time schedule. A common example of time-based maintenance involves changing the engine oil in an automobile every three months or three thousand miles, regardless of the condition of the oil to ensure that the oil is changed before its properties have degraded below minimum acceptable levels. Time-based maintenance can, therefore, lead to disposal of the oil before its useful life has ended or overuse of the oil leading to wear on the engine. Conversely, condition-based maintenance involves maintaining or changing a fluid only when certain conditions exist. For example, a fluid may be changed when the viscosity of the fluid is greater than a pre-defined value or less than a pre-defined value. Condition-based maintenance can, therefore, lead to cost savings by tailoring maintenance of a fluid to its useful life, rather than a fixed time schedule.

Acoustic wave sensing devices have been used to determine properties of a material (e.g., using surface acoustic wave or bulk acoustic wave devices). These types of devices commonly employ delay line measurements or methods. In such devices, an operating voltage is applied across input and output transducers that are coupled to (e.g., mounted on) a piezoelectric material. For example, an oscillatory operating voltage (i.e., input signal) applied to an input transducer induces a mechanical perturbation in the piezoelectric material that is measurable as an output signal by the output transducer. In delay line devices, the operating voltage can be applied for a finite time and then turned off, creating a finite oscillating wave that attenuates with time and distance as it travels. The output signal also experiences a dispersion (or smearing effect) and a time delay (with respect to the input signal) based, in part, on energy dissipation as the finite oscillating wave propagates through the piezoelectric material. Coupling a fluid to the piezoelectric material causes additional attenuation, frequency shift and time delay to occur to the oscillating wave.

Delay line measurements using acoustic devices are susceptible to reflections of the oscillating wave. More particularly, a portion of the oscillating wave generated by the input transducer interferes with a boundary of the material and is reflected back toward the input transducer. Reflection can cause interference that reduces the sensitivity of the sensor. One known method of reducing reflections and associated interference is to employ an acoustic-absorbing material in the device to absorb reflections and minimize their effect on measurement accuracy. Another drawback of certain acoustic wave devices is that they operate at relatively high frequencies (e.g., greater than 10 MHz). For example, higher operating frequencies generally necessitate more expensive electronics to observe electric signals and to observe fluid properties.

Resonators are one type of acoustic wave sensing device that actually exploits the constructive interference of oscillating wave reflections. For example, thickness shear mode ("TSM") devices use in-plane compression waves through a material (e.g., a quartz crystal) to create a resonance condition. A quartz-crystal microbalance ("QCM") device is one type of TSM device. QCM devices employ electrodes on opposing sides of a quartz disk such that a voltage applied across the electrodes induces a shear motion in the material. Shear motion in the material is measurable as the in-plane motion is projected onto the surfaces of the disk. The shear motion is affected by mass-loading of the surface of the device (e.g., by interacting a fluid with the surface of the device). The fluid slows or damps the shear motion in the device, which can be measured to infer fluid properties. TSM devices can operate in the relatively-low frequency range of under 10 MHz. However, a drawback of TSM devices is that their response depends on the boundary condition between the surface of the material (e.g., quartz disk) and the fluid. Because TSM devices use shear forces to couple with the fluid, conditions that reduce drag or cause slipping at the surface or interface (e.g., a surfactant or detergent additive in the fluid) hinder coupling. More particularly, a surface condition conducive to slipping reduces viscous drag on the surface of the material or reduces the effect of drag on the surface of the material, which decreases the accuracy of the measurement of fluid properties. Additionally, acoustic coupling of the TSM to the fluid results in disturbances in the fluid that travel ultrasonically (i.e., greater than the speed of sound) through the fluid. Waves propagating through a TSM device also travel ultrasonically. Waves having a wave velocity greater than the speed of sound associated with the fluid experience radiative loss from the surface that is in contact with the fluid. Radiative loss increases the complexity of measurement and reduces the accuracy of such devices.

Hence, there is a need for a method of measuring fluid properties more accurately. There is also a need for a more robust sensing device that can be used to determine fluid properties in the relatively low frequency domain or with reduced sensitivity to the boundary condition between the device and the fluid.

SUMMARY

The invention overcomes these shortcomings by measuring properties of fluids with reduced coupling of the sensing device to the fluid. The invention can operate in the relatively low-frequency range. The method of the invention reduces dissipative or radiative loss due to acoustic coupling of a boundary with the fluid, for example by employing standing waves associated with velocity lower than the speed of sound in the fluid. The invention realizes increased accuracy of a measured output signal by reducing effects of mechanical wave interference in the device. The invention more accurately measures fluid properties, such as viscosity and density. The invention also involves a robust, low-cost method of measuring fluid properties that can be used with a variety of fluids, including liquids, and that can be employed in devices for in situ sensing (e.g., immersion in a liquid).

The invention, in one aspect relates to a method for determining viscosity of a fluid. The method involves interacting the fluid with a standing wave in a first state to establish the standing wave in a second state, analyzing an electric signal associated with the standing wave to determine a characteristic associated with the second state, and determining the viscosity of the fluid by comparing the characteristic with a function that associates a plurality of viscosities with a corresponding plurality of characteristics. The characteristic includes a maximum phase slope of at least part of the electric signal, a phase slope associated with a resonant frequency, or both. In some embodiments, the wave speed associated with the standing wave is less than the speed of sound in the fluid. In some embodiments in which a wave speed associated with the standing wave is less than the speed of sound in the fluid, the characteristic is a maximum magnitude of at least a part of the electric signal, the magnitude of the electric signal associated with the resonant frequency, or both. The function can be a calibration function that associates a plurality of known viscosities with a plurality of known characteristics.

In some embodiments, the density of the fluid is determined by comparing the resonant frequency with a second function that associates a plurality of densities with a corresponding plurality of resonant frequencies. The second function can be a calibration function that associates a plurality of known densities with a corresponding plurality of known resonant frequencies. In some embodiments the viscosity is the dynamic viscosity of the fluid, and the method involves determining the kinematic viscosity of the fluid by relating the density of the fluid and the dynamic viscosity. In some embodiments the viscosity is the kinematic viscosity of the fluid, and the method involves determining the dynamic viscosity of the fluid by relating the density of the fluid and the kinematic viscosity of the fluid. Functions associated with the method can include, for example, a lookup table or a mathematical function.

One feature involves analyzing an electric signal associated with the second state. In some embodiments, analyzing includes conducting at least a first sweep through a bandwidth of frequencies of the standing wave to determine at least two phase values associated with at least two corresponding frequency values of the second state and providing a phase function for relating each of the phase values to the at least two frequency values such that the maximum of the phase slope is defined as a phase value at which a derivative of the phase function with respect to frequency is maximum. In some embodiments, analyzing the electric signal includes conducting at least a first sweep through a bandwidth of frequencies of the standing wave to locate the resonant frequency, determining the phase value or phase slope value associated with the resonant frequency, and defining the maximum of the phase slope as the phase value or phase slope associated with the resonant frequency. In some embodiments, the electric signal is produced by an acoustic wave device (e.g., a flexural plate wave device). In some embodiments, interacting can involve providing one or more tone bursts to an acoustic wave device to generate the standing wave. In some embodiments of the invention, determining the viscosity of the fluid involves comparing the temperature of the fluid with a second function that associates a plurality of temperatures with a second corresponding plurality of viscosities.

In another aspect, the invention relates to a method for determining a viscosity of a fluid. The method involves interacting a fluid with a standing wave in a first state to establish the standing wave in a second state, and the wave speed associated with the standing wave is less than the speed of sound in the fluid. The method also involves analyzing an electric signal associated with the standing wave to determine a characteristic associated with the second state where the characteristic includes a maximum magnitude of at least a part of the electric signal, a magnitude of at least part of the electric signal associated with a resonant frequency of the electric signal, or both (i.e., a maximum magnitude of at least part of an electric signal associated with the resonant frequency of the electric signal). The method also involves determining a viscosity of the fluid by comparing the characteristic associated with the second state with a function that associates a plurality of viscosities with a corresponding plurality of characteristics.

In some embodiments, the analyzing step includes conducting at least a first sweep through a bandwidth of frequencies of the standing wave to determine at least two magnitude values associated with at least two corresponding frequency values of the second state and providing a magnitude function for relating each of the at least two corresponding frequency values to the at least two magnitude values such that the resonant frequency is defined as a frequency value at which a derivative with respect to frequency of the magnitude function is approximately zero (i.e., approximately a relative extreme). In some embodiments, analyzing also involves conducting at least a first sweep through a bandwidth of frequencies of the standing wave to locate the resonant frequency, determining a magnitude value associated with the resonant frequency, and defining the characteristic as that magnitude value. One advantageous feature of the present invention involves determining the viscosity of the fluid by comparing the temperature of the fluid with a second function that associates a plurality of temperatures with a second corresponding plurality of viscosities.

In another aspect, the invention relates to a method for determining density of a fluid. The method includes interacting a fluid with a standing wave in a first state to establish the standing wave in a second state, analyzing an electric signal associated with the standing wave to determine a resonant frequency associated with the second state, and determining the density of the fluid by comparing the resonant frequency with a function that associates a plurality of densities with a corresponding plurality of resonant frequencies. In some embodiments, analyzing also involves conducting at least a first sweep through a bandwidth of frequencies of the standing wave to determine at least two magnitude values associated with at least two corresponding frequency values of the second state and providing a magnitude function for relating each of the at least two frequency values to the at least two magnitude values such that the resonant frequency is defined as the frequency value at which a derivative of the magnitude function is approximately zero.

In some embodiments, analyzing also involves conducting a first sweep through a bandwidth of frequencies of the standing wave to determine at least two phase values associated with at least two corresponding frequency values of the second state and providing a phase function for relating each of the at least two corresponding frequency values to the at least two phase values such that the resonant frequency is defined as a frequency value at which a derivative of the phase function is a relative extreme. In some embodiments, determining the density of the fluid also involves comparing the temperature of the fluid with a second function that associates a plurality of temperatures with a second corresponding plurality of densities.

In one aspect, the invention provides a device for determining the viscosity of a fluid. The device includes a means for interacting a fluid with a standing wave in a first state to establish the standing wave in a second state. The device also includes a means for analyzing an electric signal associated with the second state to determine a characteristic associated with the second state. The characteristic includes a maximum phase slope of the electric signal, a phase slope associated with a resonant frequency or both. The device also includes a means for determining viscosity of the fluid by comparing the characteristic associated with the second state with a function that associates a plurality of viscosities with a corresponding plurality of characteristics.

BRIEF DESCRIPTION OF THE DRAWINGS

This invention is described with particularity in the appended claims. The above and further advantages of this invention may be better understood by referring to the following description taken in conjunction with the accompanying drawings.

DETAILED DESCRIPTION

Figure 1:
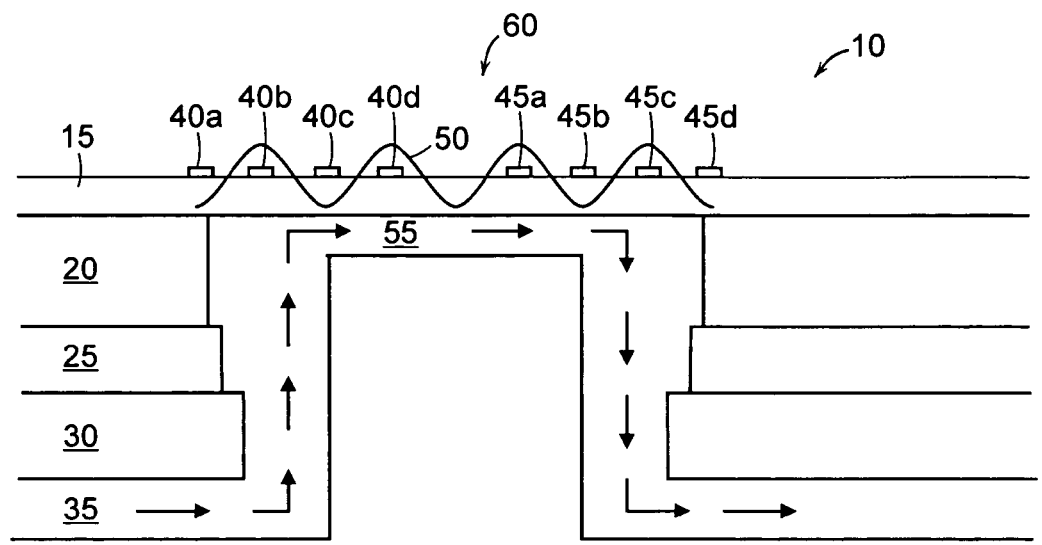
FIG. 1 is a partial schematic view of an exemplary device for determining properties of a fluid that embodies the invention.

FIG. 1 is a partial schematic view of an exemplary device for determining properties of a fluid that embodies the invention. In one embodiment, the device is an acoustic wave device. As illustrated, the device is a sensor 10 (e.g., a flexural wave plate ("FPW") sensor) that generates one or more standing waves or standing waves on a surface 15 of the sensor 10. As illustrated, the surface 15 is supported on a substrate 20, which is supported on a sealing material 25. The sealing material 25 is supported on a body 30. The body 30, sealing material 25, substrate 20 and surface 15 collectively define a fluid path 35. An input transducer 40a–40d (generally referred to herein as 40) and an output transducer 45a–45d (generally referred to herein as 45) are located on the surface 15 in an interdigitated arrangement. The input transducer 40 is coupled to a voltage source (not shown) that applies an input electric signal to the input transducer 40.

The input transducer 40 converts the electrical energy of the electric signal to mechanical energy via the inverse piezoelectric effect. The output transducer 45 is separated at a distance from the input transducer 40. The mechanical energy introduced to the surface 15 by the input transducer 40 is then measured by the output transducer 45. The output transducer 45 converts the mechanical energy into electrical energy via the piezoelectric effect. Some mechanical energy is lost to damping and radiative effects, and as such, the output electric signal has different properties than the input electric signal. In some cases, the output electric signal is frequency-shifted, of different magnitude, and out of phase with respect to the input signal. The input signal can be coupled or compared to the output electric signal using electronic circuitry to determine such effects.

In some embodiments, the voltage source supplies substantially continuous tone bursts over a long period of time relative to the frequency of the tone bursts to generate a standing wave 50 on the surface 15 from constructive interference of each of the tone bursts. The standing wave 50 is also known as a resonance condition or resonance state and is associated with one or more resonant frequencies. A "state" can refer to the electromagnetic or mechanical properties of the surface 15, the electric signal, the standing wave 50, or any combination thereof. Properties associated with a state can include, for example, a frequency (e.g., a resonant frequency), an amplitude (e.g., peak magnitude of the real part of the electric signal), a phase angle, a phase slope (with respect to frequency) and a phase or wave velocity. With respect to a standing wave 50, the term velocity refers to the phase velocity or wave velocity of traveling or propagating waves on surface 15 that constructively interfere to form the standing wave 50. A standing wave can have nodes (i.e., places along the wave at which wave properties remain constant) and antinodes (i.e., places along the wave at which the change in wave properties is greatest). In some embodiments, nodes or antinodes coincide with the interdigitated arrangement of the input transducer 40a–40d and the output transducer 45a–45d.

After a standing wave 50 has been established with respect to the surface 15, a fluid (e.g., a gas or liquid) can be passed through the fluid path 35 in a direction depicted by the arrows in FIG. 1. In a portion 55 of the flow path 35, the fluid interacts with the standing wave 50, which is in a first state prior to the interaction. In one embodiment, the first state associated with the standing wave refers to a situation where no fluid is present (e.g., in a vacuum or an unwetted or dry condition). In another embodiment, the first state refers to a situation in which a fluid is present in the portion 55 of the flow path 35. The interaction of the fluid with the standing wave 50 of the surface 15 creates a damping effect on the standing wave 50, which establishes a second state of the standing wave 50. The second state of the standing wave 50 is also a resonance condition associated with the sensor. In some embodiments, a fluid can interact with a standing wave 50 of the surface 15 from the opposite portion 60 of the surface with respect to the portion 55. An isolation layer (not shown) can be used cover the transducers 40, 45 to protect them from damage when fluids are present on the opposite portion 60. In other embodiments, the fluid interacts with a standing wave 50 of the surface 15 in both a portion 55 of the flow path 35 and the opposite portion 60 of the surface. The pressure drop across the surface 15 from the opposite face 60 to the portion 55 of the flow path 35, which can lead to higher device sensitivity.

The surface 15 of the sensor 10 can be formed of a thin piezoelectric material such as aluminum nitride, or other piezoelectric materials that can be located or deposited on the substrate 20. Other piezoelectric materials include zinc oxide or quartz (i.e., $SiO_2$). The surface 15 can be formed by processes such as sputtering or other known deposition techniques. The substrate can then be etched away or shaped by lithographic techniques.

In general, FPW devices can be configured such that a phase velocity of traveling waves that constructively interfere to form the standing wave 50 is lower than the wave speed (i.e., speed of sound) in most liquids, for example below 900 m/s. As such, less mechanical energy is lost due to damping or radiated into the fluid. Such features make FPW devices useful for biosensing applications as well as chemical sensing applications. In a particular embodiment, the surface 15 is only a few micrometers thick, thus providing increased sensitivity to mass-loading associated with, for example, the interaction of a fluid with the surface 15.

Figure 2:
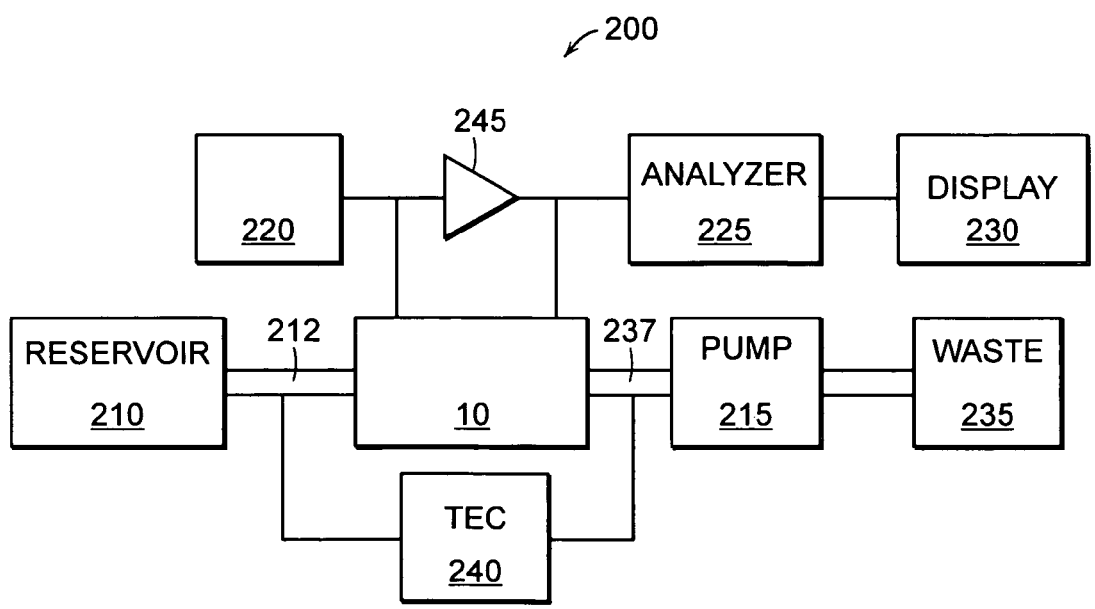
FIG. 2 is a block diagram of a system for determining properties of a fluid employing the device of FIG. 1.

FIG. 2 is a block diagram of a system for determining properties of a fluid employing the device of FIG. 1. The system 200 includes a fluid reservoir 210 pneumatically coupled via a conduit 212 (e.g., flexible tubing) to the sensor 10. The reservoir 210 acts as a local fluid supply to the sensor 10 of FIG. 1. The system 200 also includes a pump 215 (e.g., a peristaltic pump) for pulling a fluid from the reservoir 210 through the sensor 10. In this embodiment, the sensor 10 is electrically coupled to a voltage source 220 that supplies an AC voltage to the input transducer 40. The output transducer 45 of FIG. 1 is coupled to an analyzer 225 for measuring or observing electric signals associated with the sensor 10. The analyzer 225 is coupled to a display 230 such as a computer monitor for displaying the electric signal. The system 200 also includes a waste reservoir 235 for collecting fluids that have passed through the sensor 10 (or whose properties have been measured). The waste reservoir 235 is pneumatically coupled to the sensor 10 via a conduit 237 (e.g., flexible tubing). As depicted, the system 200 includes a thermoelectric cooler ("TEC") 240 operatively coupled in a feedback loop from the fluid output of the sensor 10 to conduit 212. In some embodiments, means other than a pump 215 is used to pass a fluid through the device 10, and particularly across surface 15 of FIG. 1, such as a gravity head, immersion in the fluid, or other methods of convecting fluid.

Some or all of the components of system 200 may be co-located. For example, the sensor 10 may be seated on or within the analyzer 225. In another embodiment, the analyzer 225 is a software program operating on a computer that is coupled to the display 230. In still another embodiment, the analyzer 225 is coupled (e.g., by a GPIB bus, USB bus or by a wireless connection such as Bluetooth® (Bluetooth SIG, Inc. of Washington D.C.)) to a computer that has graphical user interface software that manages the information presented on display 230. In some embodiments, the analyzer 225, for example, performs data acquisition, recording, manipulation, and presentation functions. In one embodiment, the computer software LabVIEW (National Instruments Corp. of Austin, Tex.) is the analyzer 225.

In some embodiments, the TEC 240 is mounted on a device (not shown) that houses the sensor 10. The TEC 240 maintains a generally constant temperature of fluids being processed by sensor 10. Controlling the temperature of the fluid reduces the effect that temperature fluctuations have on the electrical output of the sensor 10. For example, by increasing the temperature of a fluid, the viscosity of the fluid can be reduced before it enters the sensor 10, which beneficially reduces flow resistance of the fluid, increases surface wetting and mixing rate, and lowers pressure requirements of the pump 215. The lower pressure requirements also protects the sensor 10 and other components from potential damage or rupture. In this embodiment, TEC 240 includes a temperature controlled conduit (e.g., flexible tubing) disposed between the pump 215 and the sensor 10 in a feedback loop for providing temperature control and observation. Temperature is controlled by a temperature feedback element (e.g., a thermistor mounted to the TEC 240 or deposited by lithography onto the surface 15 of the sensor 10) or a resistance temperature detector thermally coupled to the sensor 10.

In one embodiment, the analyzer 225 also functions as the voltage source 120. The analyzer 225 can be a vector network analyzer, a spectrum analyzer, or another device capable of displaying or analyzing an electric signal in the frequency domain. In this embodiment, the analyzer 225 supplies a radio frequency sine wave voltage (i.e., input voltage) to the input transducer 40 of the sensor 10 (e.g., by using a direct digital synthesizer) and measures the voltage on the output transducer 45 (i.e., output signal) as frequency is swept across a bandwidth of frequencies that can include the resonant frequencies of the sensor 10. The output electric signal is recorded and analyzed (e.g., phase and magnitude of the output voltage are determined) as a function of the input signal (e.g., voltage and frequency). More particularly, the phase and magnitude of the output signal is compared to the phase and magnitude of the input signal over the frequency domain. In the illustrated embodiment, circuitry 145 (e.g., a feedback amplifier) is employed to provide or compare an output signal of the sensor 10 relative to the input signal. In other embodiments, the output signal can be compared to a reference signal (i.e., not necessarily the input signal).

Figure 3:
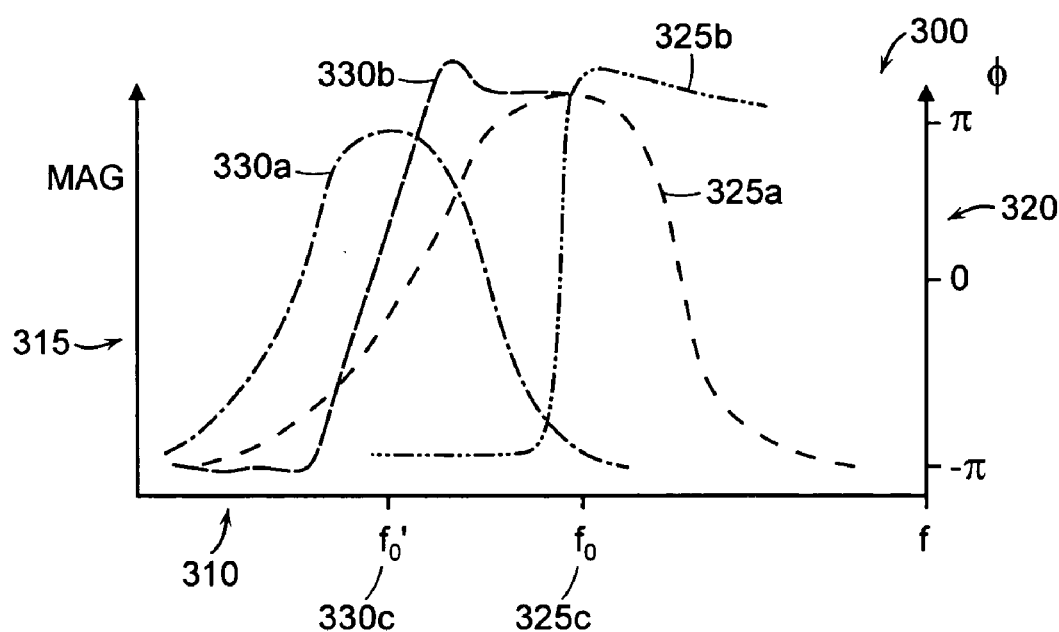
FIG. 3 is a graphical representation of an electric signal, including phase angle and magnitude versus frequency, associated with a standing wave according to the invention.

FIG. 3 is a graphical representation of an electric signal, including phase angle and magnitude versus frequency, associated with a standing wave according to the invention. The analyzer 225 of FIG. 2 can display magnitude and phase information in the frequency domain as a graph 300. In the illustrated embodiment, the frequency of the electric signal is depicted along a horizontal axis 310, while the magnitude axis 315 and phase axis 320 are vertical. In one embodiment, a standing wave is established in a first state 325a–c(generally referred to herein as 325). A standing wave in the first state 325 has a magnitude profile 325a associated with the real part of an electric signal and a phase profile 325b associated with the imaginary part of the electric signal. A standing wave in a second state 330 has a magnitude profile 330a and a phase profile 330b.

The first state 325 is associated with a resonant frequency 325c, and the second state is also associated with a resonant frequency 330c. Resonant frequencies 325c, 330c can be associated with a peak of the magnitude profile 325a, 330a or the steepest portion of the phase profile 325b, 330b, or both. Changes to the profiles 330a, 330b of the electric signal between the first state 325 and the second state 330 can be caused by interaction of the fluid with the standing wave 325, particularly effects caused by the viscosity or density of the fluid that is interacting with the standing wave 325.

In particular, the relationship between the standing wave 325, 330 on an FPW device and fluid properties (e.g., viscosity and density) is mathematically determined by examining the equations of traveling waves:

$$A(x,t)=A_0 e^{-\alpha x}\cos(\beta x-2\pi ft+\phi) \quad \text{Equation 1}$$

Equation 1 represents a wave traveling over the surface 15 of FIG. 1, where:

$A_0$ is the standing wave amplitude at the location in which standing waves are generated (i.e., the input transducer);

$\alpha$ is the wave attenuation (loss or damping due to viscosity of the fluid and other factors) in units of $m^{-1}$;

$\beta$ is equal to $2\pi/\lambda$, where $\lambda$ is wavelength. At a resonance condition, $\lambda$ is approximately equal to P, the distance between fingers of the interdigitated transducers, as determined during sensor fabrication; therefore, $\beta=2\pi/P$ is a known constant at the resonant frequency.

f is the temporal frequency of the traveling waves. At resonance, $\lambda \sim P$ and $f \sim f_0$, where $f_0$ is the resonant frequency; and $\phi$ is a phase angle.

A standing wave is represented by a linear combination or superposition of traveling waves. A traveling wave may be reflected from one or more boundaries to interact with itself to form standing waves. The resonant frequency and the loss due to damping in a low viscosity fluid are represented below with respect to Equations 2 and 3.

$$f_0 = \frac{2\pi}{P^2} \sqrt{\frac{D_1}{M + \rho\delta + \frac{1}{2}\sqrt{\rho\eta/\pi f}}} \quad \text{Equation 2}$$

M is mass density of the surface 15 or material on which the standing wave is disposed, a constant;

$\rho$ is the density of the fluid interacting with the standing wave 325;

$\eta$ is the dynamic viscosity of the fluid;

d is the skin depth of standing wave motion in the fluid; and $D_1$ is the stiffness of the surface 15, a constant value.

$$\alpha \approx \frac{(\pi f)^{\frac{3}{2}} \sqrt{\rho\eta}}{D_2} \quad \text{Equation 3}$$

$D_2$ is a stiffness constant related to P and $D_1$ of Equation 2.

Equation 1 describes a one-dimensional traveling wave whose properties can be measured at any point along a one-dimensional axis. For a standing wave or resonator, a different quantity, "Q" or quality factor can be measured. Q is the ratio of energy stored to energy dissipated during each time cycle of the standing wave and can be measured by comparing the input electric signal to the output electric signal as discussed above. Q can be related to the loss due to damping, $\alpha$, by Equation 4:

$$Q = \frac{\beta}{2\alpha} = \frac{\pi}{\alpha P} \quad \text{Equation 4}$$

Referring to Equations 2 and 3, in the presence of a viscous fluid, two measurable effects occur. First, the resonant frequency of the standing wave (and thus, the associated electric signal) is decreased due to viscous drag, represented in Equation 2 by the term $\frac{1}{2}\sqrt{\rho\eta/\pi f}$. Second, loss due to damping, $\alpha$, increases due to internal friction (i.e., viscosity) of the fluid. Loss due to viscosity is proportional to the square-root of the viscosity (more particularly, to the viscosity-density product, $\rho\eta$). In piezoelectric materials, the output electric signal represents mechanical properties of the standing wave, such as displacement (e.g., amplitude or magnitude) and frequency. In one embodiment, the invention provides for determination of the kinematic viscosity of the fluid. Kinematic viscosity, $\mu$, is related to dynamic viscosity, $\eta$, and density, $\rho$, by Equation 5:

$$\mu = \frac{\eta}{\rho} \quad \text{Equation 5}$$

Referring to Equation 5, measuring any two of the quantities in the equation permits for determining the third quantity. For example, by measuring or determining $\mu$ and $\rho$ of a fluid, $\eta$ is determined. Similarly, by determining or measuring $\eta$ and $\rho$ of a fluid, $\mu$ can be determined. Additionally, by determining $\mu$ and $\eta$ of a fluid, $\rho$ can be determined.

In general, properties of a fluid are determined by interacting a fluid with a standing wave in a first state 325 to establish a standing wave in a second state 330. An electric signal associated with the standing wave in a second state 330 is analyzed in the frequency domain to determine a characteristic (e.g., a phase characteristic or a magnitude characteristic) associated with the second state 330. Fluid properties are determined by comparing the characteristic with a function that associates one or more fluid properties with one or more corresponding characteristics. The invention will be described in terms of particular characteristics corresponding to particular fluid properties. However, as the Equations above indicate, derivations and manipulations of the characteristics and fluid properties can be made without departing from the scope of the invention, for example, by common mathematical operations such as multiplication or inversion (i.e., a reciprocal). An embodiment of the invention involves using an analyzer 225 to measure a property of the electric signal (also called a characteristic) and associating the property with the frequency at which it was measured.

Additionally, in some embodiments, the characteristic of the electric signal can be measured or tracked by the analyzer as the analyzer conducts subsequent frequency scans or sweeps. A user can select a characteristic for observation, and the analyzer can determine and provide for display of the characteristic and the frequency associated with the characteristic. The user can set parameters for the analyzer such as the bandwidth of frequencies to be swept, the number of points or "hits" to record, the characteristic to be observed, or any combination of these. Additionally, using a multi-channel analyzer, the invention allows for determining a resonant frequency according to one of the methods described below (e.g., using a characteristic related to the phase of the electric signal), and then conducting a subsequent sweep using that resonant frequency as a "center point." In this way, the resonant frequency can be tracked regardless of the characteristic of interest. More particularly, the resonant frequency can be determined with a first characteristic (e.g., related to phase) and subsequent sweeps can observe a second characteristic (e.g., magnitude). In some embodiments, more than one standing wave is generated by an array of transducers or sensors such that the standing waves have frequency values approximately equal to the resonant frequency, but slightly displaced from the resonant frequency.

Figure 4:
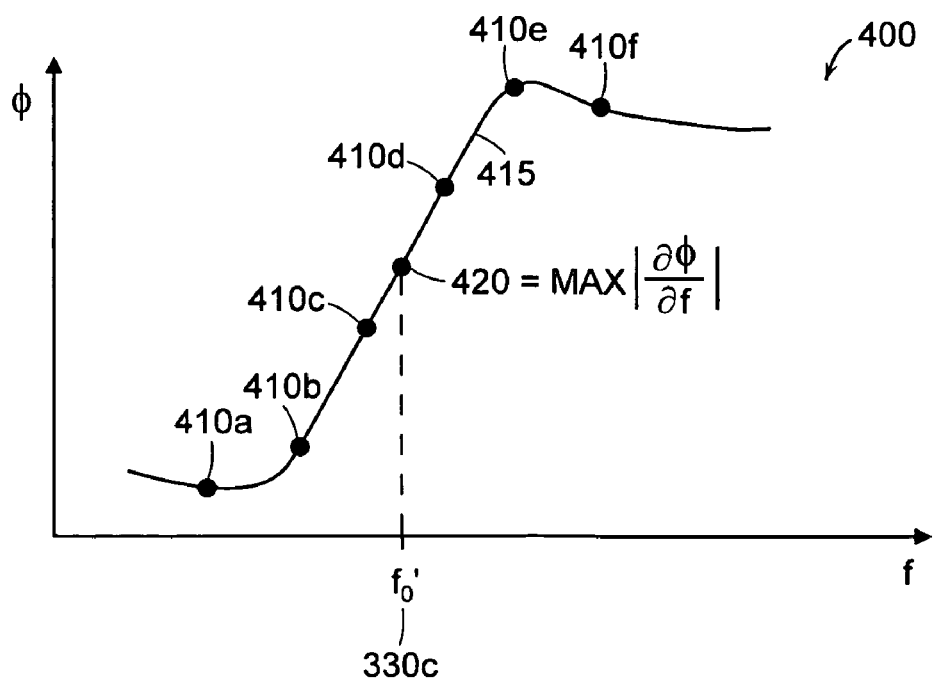
FIG. 4 is a graphical representation of phase angle versus frequency where a characteristic of the electric signal is determined, based on a method according to the invention.

FIG. 4 is a graphical representation of phase angle versus frequency where a characteristic of the electric signal is determined, based on a method according to the invention.

In the graph 400, curve 415 is related to the imaginary part 330b (not shown) of the electric signal in the second state 330 of FIG. 3. The characteristic of the electric signal of interest relates to phase values associated with corresponding frequency values of the electric signal. The resonant frequency can be determined and defined based on the curve 415. In this embodiment, the analyzer performs a sweep through a bandwidth of frequencies to locate two or more phase values (measured in degrees or radians) associated with corresponding frequency values (in units of Hertz) to form two or more ordered pairs 410a–410f (generally 410), which form discrete points in a frequency-phase space. The two or more ordered pairs 410 can be used to find the resonant frequency 330c of the second state 330. In one embodiment, a phase function is provided that relates each of the phase values to each of the corresponding frequency values. In such an embodiment, the phase function can be a fitted curve (e.g., polynomial equations of various order), a lookup table, a mathematical function, a graph, a discrete relationship consisting of line segments between ordered pairs, or any other way of relating phase values to frequency values or vice versa. As depicted, the phase function is fitted to the ordered pairs 410 over a bandwidth of frequencies and results in curve 415. In one embodiment, curve 415 is a sixth-order polynomial fit. Other fitted curves will be apparent to the skilled artisan.

In this embodiment, the phase function 415 is differentiable with respect to frequency. The resonant frequency 330c is defined to correspond to the phase value 420 at which the derivative of the phase function 415 with respect to the frequency is greatest (i.e., where the "phase slope" is steepest regardless of whether the function is increasing or decreasing) or has greatest magnitude. More particularly, phase slope is the change in phase values divided by the change in frequency values (i.e., $\Delta\phi/\Delta f$). When the phase function is differentiated with respect to frequency, the phase slope at a given phase value is the instantaneous rate of change of the phase with respect to frequency at that frequency value. By implication, in this embodiment the inverse or reciprocal of the phase slope is a minimum. In the illustrated embodiment, phase value 420 was determined based on the phase function 415. Alternatively, in some embodiments, the phase value 420 is determined by the analyzer. In determining the phase slope, extrapolation can be used.

In another embodiment, determining the phase function involves determining the slope between two ordered pairs (e.g., 410c–d) by comparing the ratio of the change in phase values to the change in frequency values of the two ordered pairs. This method can be used to determine the phase slope when a resonant frequency value is already defined (e.g., from a prior sweep by the analyzer). In general, as the number of ordered pairs 410a–f returned by the analyzer increases, the accuracy of the value of the resonant frequency increases. To increase accuracy, the analyzer can be configured to conduct a first sweep through a relatively wide bandwidth of frequencies to locate the resonant frequency and then conduct a second sweep through a relatively narrow bandwidth of frequencies (based on the results of the first sweep) to more accurately determine the resonant frequency. For example, a subset of the bandwidth of frequencies associated with the resonant frequency of the first sweep could be used to define the bandwidth of the second sweep. In another embodiment, after the resonant frequency has been determined, the analyzer can continue to monitor and track the resonant frequency as future fluid interactions with the surface of the sensor establish subsequent states of the standing wave.

In some embodiments, the phase slope associated with a particular resonant frequency is used to determine viscosity of the fluid. For example, the resonant frequency is determined or defined by looking at maximum phase slope or maximum magnitude of the real part of the electric signal as discussed below. The phase slope associated with the value associated with the resonant frequency is used to compare to a function to determine viscosity of the fluid. Where the phase value or phase slope is the characteristic returned by the analyzer, either the steepest phase slope or the phase slope determined by locating the resonant frequency can be used as the characteristic.

Figure 5:
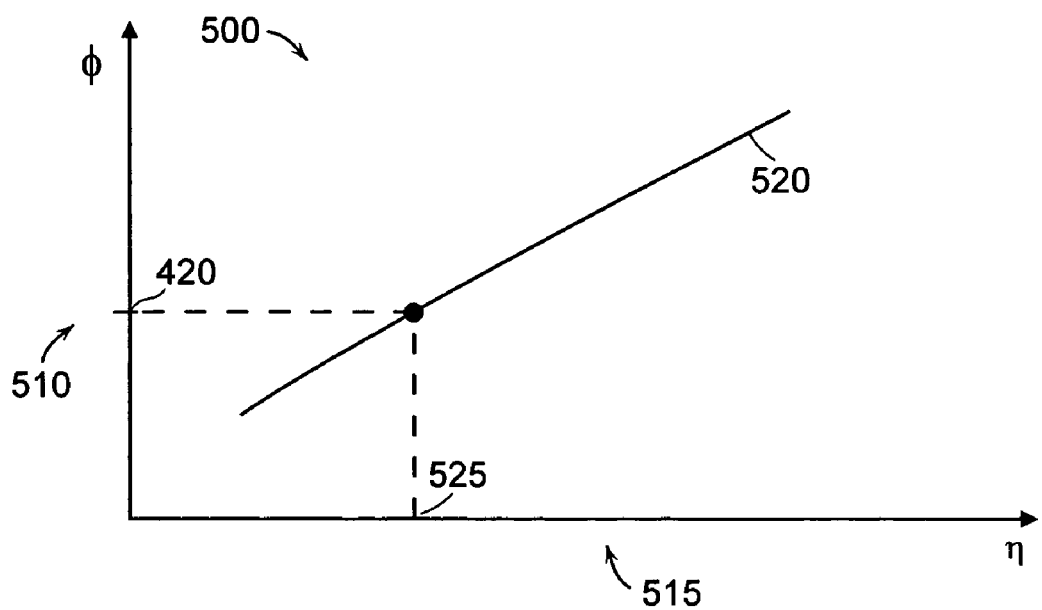
FIG. 5 is a graphical representation of phase angle versus viscosity.

FIG. 5 is a graphical representation of phase angle versus viscosity. The graph 500 depicts phase values along the vertical axis 510 and viscosity values along the horizontal axis 515. The graph 500 also depicts a graphical function 520 that relates phase values to corresponding viscosity values (also called viscosities). In this embodiment, the function 520 is substantially linear. A substantially linear function 520 occurs when the values along the vertical axis 510 are related to phase slopes, in particular the inverse of maximum phase slope values, and are plotted against the square root of dynamic viscosity values, plotted horizontally. Other functions for relating phase values and viscosities can be used (e.g., plotting phase slope values against dynamic viscosity values or against kinematic viscosity values) without departing from the scope of the invention.

In this embodiment, the phase slope value 420 of FIG. 4 is compared to the function 520 to determine a viscosity value 525 associated with that phase slope value 420. More particularly, the phase value 420 is an input into the function 520 and the viscosity value 525 is the output of the function 520. In one embodiment, the function 520 is a calibration function that associates one or more known phase values with one or more corresponding viscosity values. Such a calibration function can be empirically generated by analyzing standing waves as they interact with fluids having known viscosity values. The phase values associated with the fluids can be used to generate the calibration function (or specific points along the curve of the function). More particularly, the phase values (i.e., maximum phase slope) can be associated with the corresponding known viscosities to form ordered pairs, and the ordered pairs can be used to generate a calibration function for extrapolating viscosity values when the phase value is known or measured. In one embodiment, the calibration function is a fitted curve (e.g., sixth-order polynomial fitted function). In other embodiments, the function is a theoretical algebraic function (e.g., an equation) that does not require associating measured phase values with viscosities of known fluids. In other embodiments, the function 520 can be a lookup table or a graph.

Figure 6:
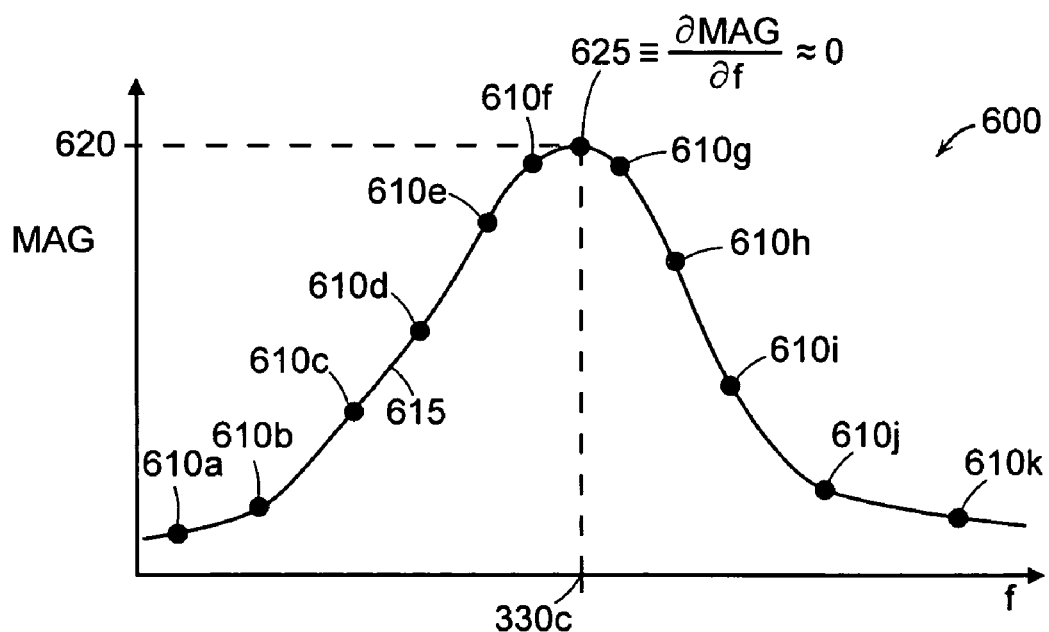
FIG. 6 is a graphical representation of the magnitude of an electric signal versus frequency, where a characteristic of the electric signal is determined based on a method according to the invention.

FIG. 6 is a graphical representation of the magnitude of an electric signal versus frequency, where a characteristic of the electric signal is determined based on a method according to the invention. In the graph 600, curve 615 is related to the real part 330a (not shown) of the electric signal in the second state 330 of FIG. 3. In this embodiment, the characteristic of the electric signal of interest relates to magnitude values (e.g., maximum magnitude) associated with corresponding frequency values of the electric signal. The resonant frequency can be determined based on the curve 615. In this embodiment, the analyzer performs a sweep through a bandwidth of frequencies to locate two or more magnitude values (in units of dB or Volts depending on the output signal that is analyzed) associated with corresponding frequency values (in units of Hertz) to form two or more ordered pairs 610a–610k (generally 610), which form discrete points in a frequency-magnitude space. The two or more ordered pairs 610 can be used to find the resonant frequency 330c of the second state 330 of FIG. 3. In one embodiment, a magnitude function is provided that relates each of the magnitude values to each of the corresponding frequency values. The magnitude function can be a fitted curve (e.g., polynomial equation of various order), a lookup table, a mathematical function, a graph, a discrete relationship consisting of line segments between ordered pairs, or any other way of relating magnitude values to frequency values or vice versa. As depicted, the magnitude function is fitted to the ordered pairs 610 over a bandwidth of frequencies and results in curve 615. In one embodiment, curve 615 is a sixth-order polynomial fit. Other fitted curves will be apparent to the skilled artisan.

In this embodiment, the magnitude function 615 is differentiable with respect to frequency. The resonant frequency 330c is defined to correspond to the magnitude value 620 at which the derivative of the magnitude function 615 with respect to the frequency is approximately zero (i.e., a relative maximum or minimum of the magnitude function) 625. Such a magnitude value can be also referred to as the "maximum magnitude." In the illustrated embodiment, magnitude value 620 was determined based on the magnitude function 615. Alternatively, in some embodiments, the magnitude value 620 is determined by the analyzer. In some embodiments, the magnitude value 620 is extrapolated from the magnitude function (e.g., curve 615). In general, as the number of ordered pairs 610a–610k returned by the analyzer increases, the accuracy of the value of the resonant frequency increases.

To increase accuracy, the analyzer can be configured to conduct a first sweep through a relatively wide bandwidth of frequencies to locate the resonant frequency and then conduct a second sweep through a relatively narrow bandwidth of frequencies (based on the results of the first sweep) to more accurately determine the resonant frequency by returning the same number of points or ordered pairs 610 over a narrower bandwidth. For example, a subset of the bandwidth of frequencies of the resonant frequency of the first sweep can be used to define the bandwidth of the second sweep. In some embodiments, after the resonant frequency has been determined, the analyzer can continue to monitor and track the resonant frequency as future fluid interactions with the surface of the sensor establish subsequent states of the standing wave. Such tracking allows observation of shifts or other effects to the resonant frequency as different fluids interact with the standing wave even as other characteristics are observed.

In some embodiments, the magnitude value associated with a particular resonant frequency is used to determine the viscosity of the fluid. For example, the resonant frequency is determined or defined (i.e., by looking at maximum phase slope or maximum magnitude), and the magnitude value associated with the frequency value associated with the resonant frequency is used to compare to a function to determine viscosity of the fluid. Where the magnitude value is the characteristic returned by the analyzer, either the maximum magnitude or the magnitude determined by locating the resonant frequency can be used as the characteristic.

Figure 7:
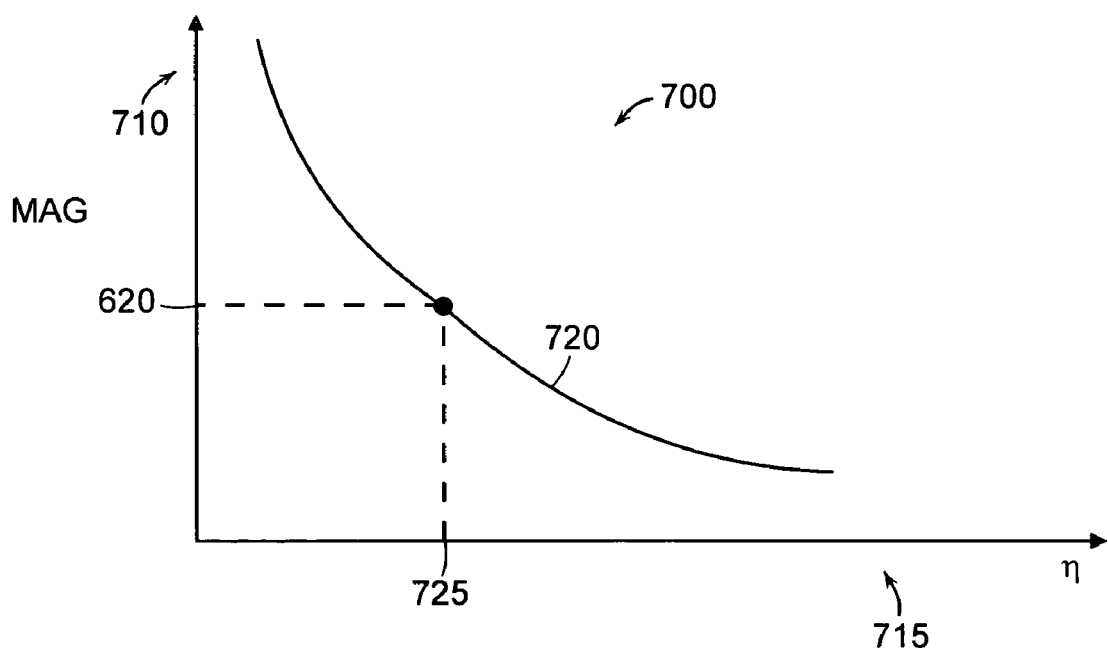
FIG. 7 is a graphical representation of magnitude values of an electric signal versus viscosity.

FIG. 7 is a graphical representation of magnitude values of an electric signal versus viscosity. The graph 700 depicts magnitude values along the vertical axis 710 and viscosity values along the horizontal axis 715. The graph 700 also depicts a curve 720 that relates magnitude values to corresponding viscosity values (also called viscosities). In this embodiment, the curve 720 is monotonically decreasing. A decreasing curve 720 occurs when the magnitude values along the vertical axis 710 are maximum magnitudes and are plotted against dynamic viscosity values, plotted horizontally. Other functions for relating magnitude values and viscosities can be used without departing from the scope of the invention. In some embodiments employing other magnitude values and viscosities changes the shape of curve 720. For example, plotting the reciprocal of maximum magnitudes vertically and dynamic viscosities horizontally results in a monotonically increasing curve 720.

In this embodiment, the magnitude value 620 of FIG. 6 is compared to the curve 720 to determine a viscosity value 725 associated with that magnitude value 620. More particularly, the magnitude value 620 is an input for the function, and the viscosity is the output of the function. In one embodiment, the function is a calibration function that associates one or more known magnitude values with one or more corresponding viscosity values. Such a calibration function can be empirically generated by analyzing standing waves as they interact with specific fluids having known viscosity values. The magnitude values associated with the specific fluids can be used to generate that calibration function (or specific points along the curve 720 of the function. More particularly, the magnitude values (i.e., maximum magnitude) can be associated with the corresponding known viscosities to form ordered pairs, and the ordered pairs can be used to generate a calibration function for extrapolating or determining viscosity values when the magnitude characteristic is known or measured. In one embodiment, the calibration function is a fitted curve (e.g., sixth-order polynomial). In other embodiments, the function 720 is a theoretical algebraic function that does not require associating measured or analyzed magnitude values with viscosities of known fluids (i.e., using the analyzed magnitude value as an input for a mathematical equation). In other embodiments, the function 720 can be a lookup table or a graph.

Figure 8:
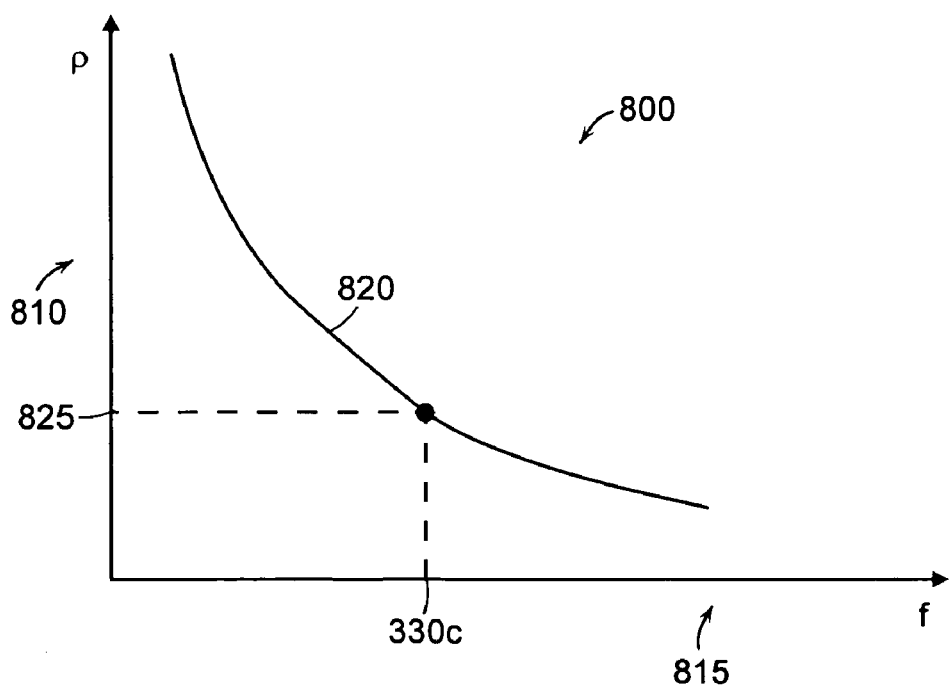
FIG. 8 is a graphical representation of resonant frequency versus density.

FIG. 8 is a graphical representation of resonant frequency versus density. The graph 800 depicts density values along the vertical axis 810 and frequency values along the horizontal axis 815. The graph 800 also depicts a graphical function 820 for relating density values (also called densities) to corresponding frequency values. As depicted, the function 820 is a decreasing function. This depiction of function 820 is exemplary only. Alternatively, function 820 appears differently based on the scale of the vertical and horizontal axes 810, 815.

In an embodiment, the resonant frequency 330c associated with the standing wave in the second state of FIGS. 3,4 and 6 is compared to the function 820 to determine a density value 825 associated with the resonant frequency 330c. In one embodiment, the function 820 is a calibration function that associates one or more known or measurable density values with one or more corresponding frequency values. A calibration function can be generated by analyzing standing waves as the standing waves interact with multiple fluids having known density values. In such an embodiment, the resonant frequency is analyzed using the methods discussed above (i.e., the phase slope method or the magnitude method). The determined resonant frequency values are associated with the known density of the fluid to form a portion of the calibration function. More particularly, the resonant frequencies can be associated with the corresponding known densities to form ordered pairs, and the ordered pairs can be used to generate a calibration function such as a fitted curve (e.g., sixth-order polynomial). In some embodiments, the function 820 is a theoretical algebraic function that does not require associating frequencies with densities of known fluids (e.g., using the resonant frequency as an input for a mathematical equation). In other embodiments, the function 820 can be a lookup table or a graph.

In some embodiments, a resonant frequency is determined using either the phase values or magnitude values as described above. The resonant frequency can determine the density of the fluid that is interacting with the standing wave. The resonant frequency can then be used to determine the maximum phase slope (or other phase value) or the maximum magnitude, either of which can be used to determine the viscosity of the fluid. The determined density and determined viscosity can be used to calculate a derived viscosity of the fluid according to the relationship of Equation 5 and as discussed above. For example, if the density and dynamic viscosity are determined, the kinematic viscosity can be calculated. Likewise, if the density and kinematic viscosity are determined, the dynamic viscosity can be calculated.

Figure 9:
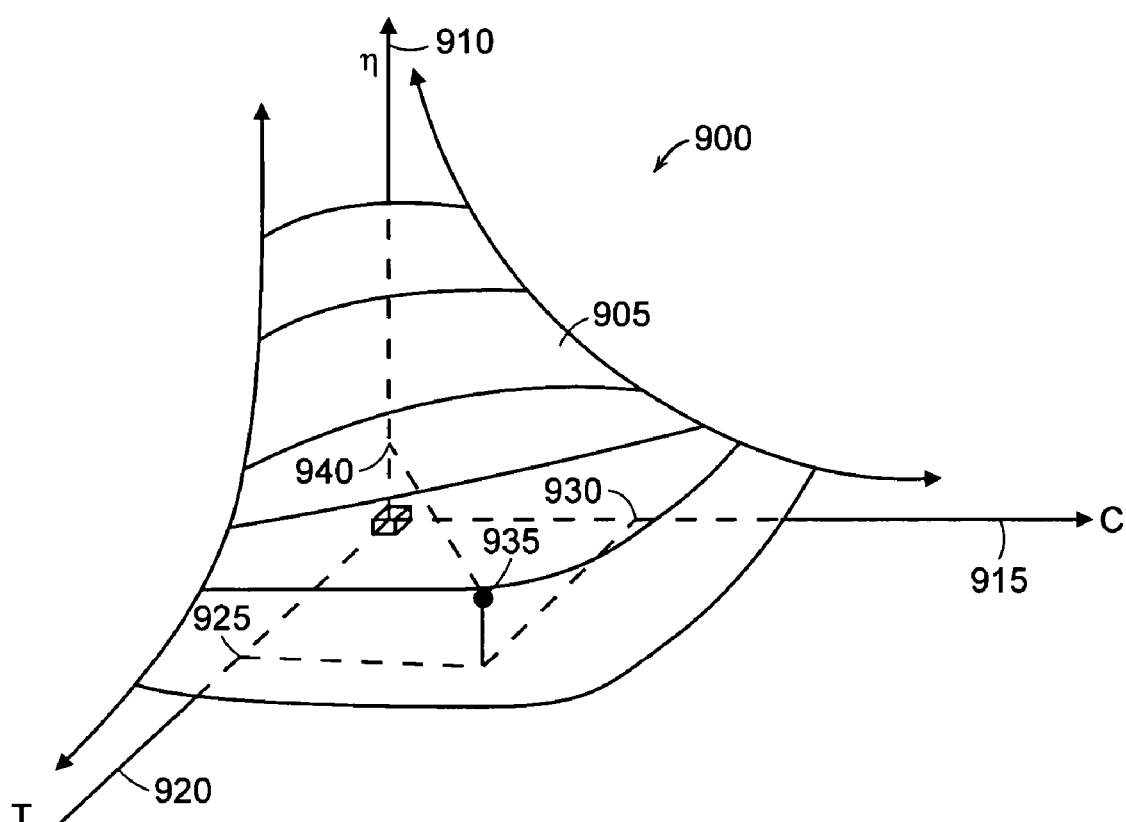
FIG. 9 is a three-dimensional graphical representation of the characteristic and temperature versus frequency.

FIG. 9 is a three-dimensional graphical representation of the characteristic and temperature versus frequency. The graph 900 depicts an exemplary three-dimensional surface 905. The vertical axis 910 of the graph 900 represents viscosity values. The horizontal axis 915 of the graph 900 represents characteristic values of the standing wave in the second state (e.g., maximum phase slope values, phase values, maximum magnitude values, or other values associated with the resonant frequency). The orthogonal axis 920 represents temperature values associated with the fluid that interacts with the standing wave. The surface 905 is a graphical depiction of a multivariable function that couples a first function that relates viscosity values to corresponding characteristic values and a second function that relates viscosity values to corresponding temperature values. The surface 905 is exemplary in nature and does not represent any particular multivariable function. The shape of the surface can change depending on the quantities and scale along the axes 910, 915, 920 (e.g., which characteristic is used to determine viscosity and the units of measurement associated therewith).

In some embodiments, a temperature value 925 of the fluid is determined through temperature-sensing techniques (e.g., by a thermometer) before, during, or after interacting the fluid with the standing wave. The temperature value 925 is an input into the function that relates temperature and characteristic values to corresponding viscosity values. In such an embodiment of the invention, a characteristic value 930 is determined by any of the methods described above with respect to FIGS. 4 and 6 (e.g., a phase slope method, magnitude method, or phase or magnitude values associated with the resonant frequency). The horizontal axis 915 is altered (e.g., recalibrated or renormalized) to compensate for the characteristic of interest, and a resultant change to the surface 905 occurs as well. In a particular embodiment, the temperature value 925 and the characteristic value 930 are associated with a viscosity value, represented as an ordered triplet 935 on the surface 905. More particularly, temperature and the characteristic are inputs into the multivariable function, and the viscosity is the output of the function. The function can be a surface, an algebraic expression, a lookup table, a graph, or any other means for relating two variables to a fluid property. In some embodiments, the first function and the second function are not coupled into a multivariable function. Viscosity of a fluid has a temperature-dependent component that varies as temperature changes. An advantageous feature of this embodiment allows the invention to be employed in a variety of in situ applications for determining viscosity of fluids for which controlling temperature is not desirable, feasible, or economical.

While the invention has been particularly shown and described with reference to specific embodiments, it should be understood by those skilled in the art that various changes in form and detail may be made therein without departing from the spirit and scope of the invention as defined by the appended claims.

What is claimed is:

1. A method for determining viscosity of a fluid comprising:
   interacting the fluid with a standing wave in a first state to establish the standing wave in a second state;
   analyzing an electric signal associated with the standing wave to determine a characteristic associated with the second state, wherein the characteristic comprises at least one of a maximum phase slope of at least a part of the electric signal, a phase slope associated with a resonant frequency, or both; and
   determining the viscosity of the fluid by comparing the characteristic associated with the second state with a function that associates a plurality of viscosities with a corresponding plurality of characteristics.

2. The method of claim 1, wherein a wave speed associated with the standing wave is less than the speed of sound in the fluid.

3. The method of claim 1, wherein the function is a calibration function that associates a plurality of known viscosities with a corresponding plurality of known characteristics.

4. The method of claim 1, wherein the function comprises a lookup table or a mathematical formula.

5. The method of claim 1, wherein analyzing further comprises:
   conducting at least a first sweep through a bandwidth of frequencies of the standing wave to determine at least two phase values associated with at least two corresponding frequency values of the second state; and
   providing a phase function for relating each of the phase values to the at least two frequency values, wherein the maximum of the phase slope is defined as a phase value at which a derivative of the phase function is a relative extreme.

6. The method of claim 1, wherein analyzing further comprises:
   conducting at least a first sweep through a bandwidth of frequencies of the standing wave to locate the resonant frequency;
   determining a phase value associated with the resonant frequency; and
   defining the maximum of the phase slope as the phase value associated with the resonant frequency.

7. The method of claim 1, wherein interacting further comprises providing one or more tone bursts to an acoustic wave device to generate the standing wave.

8. The method of claim 1, wherein determining viscosity of the fluid comprises comparing the temperature of the fluid with a second function that associates a plurality of temperatures with a second corresponding plurality of viscosities.

9. The method of claim 1, wherein the electric signal is produced by an acoustic wave device.

10. The method of claim 9, wherein the acoustic wave device is a flexural plate wave device.

11. The method of claim 1, further comprising:
  determining density of the fluid by comparing the resonant frequency with a second function that associates a plurality of densities with a corresponding plurality of resonant frequencies.

12. The method of claim 11, wherein the second function is a calibration function that associates a plurality of known densities with a corresponding plurality of known resonant frequencies.

13. The method of claim 11, wherein the viscosity is the dynamic viscosity of the fluid, and further comprising:
  determining the kinematic viscosity of the fluid by relating the density of the fluid and the dynamic viscosity of the fluid.

14. The method of claim 4, wherein the viscosity is the kinematic viscosity of the fluid, and further comprising:
  determining the dynamic viscosity of the fluid by relating the density of the fluid and the kinematic viscosity of the fluid.

15. A method for determining viscosity of a fluid comprising:
  interacting the fluid with a standing wave in a first state to establish the standing wave in a second state, wherein a wave speed associated with the standing wave is less than the speed of sound in the fluid;
  analyzing an electric signal associated with the standing wave to determine a characteristic associated with the second state, wherein the characteristic comprises a maximum magnitude of at least a part of the electric signal associated with a resonant frequency of the electric signal; and
  determining viscosity of the fluid by comparing the characteristic associated with the second state with a function that associates a plurality of viscosities with a corresponding plurality of characteristics.

16. The method of claim 15, wherein analyzing further comprises:
  conducting at least a first sweep through a bandwidth of frequencies of the standing wave to determine at least two magnitude values associated with at least two corresponding frequency values of the second state; and
  providing a magnitude function for relating each of the at least two corresponding frequency values to the at least two magnitude values, wherein the resonant frequency is defined as a frequency value at which a derivative with respect to frequency of the magnitude function is approximately zero.

17. The method of claim 15, wherein determining the viscosity of the fluid comprises comparing the temperature of the fluid with a second function that associates a plurality of temperatures with a second corresponding plurality of viscosities.

18. A method for determining density of a fluid comprising:
  interacting the fluid with a standing wave in a first state to establish the standing wave in a second state;
  analyzing an electric signal associated with the standing wave to determine a resonant frequency associated with the second state; and
  determining density of the fluid by comparing the resonant frequency with a function that associates a plurality of densities with a corresponding plurality of resonant frequencies.

19. The method of claim 18, wherein analyzing further comprises:
  conducting at least a first sweep through a bandwidth of frequencies of the standing wave to determine at least two magnitude values associated with at least two corresponding frequency values of the second state; and
  providing a magnitude function for relating each of the at least two frequency values to the at least two magnitude values, wherein the resonant frequency is defined as a frequency value at which a derivative of the magnitude function is approximately zero.

20. The method of claim 18, wherein analyzing further comprises:
  conducting at least a first sweep through a bandwidth of frequencies of the standing wave to determine at least two phase values associated with at least two corresponding frequency values of the second state; and
  providing a phase function for relating each of the at least two corresponding frequency values to the at least two phase values, wherein the resonant frequency is defined as a frequency value at which a derivative of the phase function is a relative extreme.

21. The method of claim 18, wherein determining the density of the fluid comprises comparing the temperature of the fluid with a second function that associates a plurality of temperatures with a second corresponding plurality of densities.

22. An apparatus for determining viscosity of a fluid, the device comprising:
  a means for interacting a fluid with a standing wave in a first state to establish the standing wave in a second state;
  a means for analyzing an electric signal associated with the standing wave to determine a characteristic associated with the second state, wherein the characteristic comprises at least one of a maximum phase slope, a phase slope associated with a resonant frequency, or both;
  a means for determining viscosity of the fluid by comparing the characteristic associated with the second state with a function that associates a plurality of viscosities with a corresponding plurality of characteristics.

* * * * *